United States Patent
Suri et al.

(10) Patent No.: US 8,644,908 B2
(45) Date of Patent: Feb. 4, 2014

(54) IMAGING DEVICE FOR FUSED MAMMOGRAPHY WITH INDEPENDENTLY MOVEABLE IMAGING SYSTEMS OF DIFFERENT MODALITIES

(75) Inventors: Jasjit Suri, Roseville, CA (US); Cara Coad, Boulder, CO (US); Idris A. Elbakri, Winnipeg (CA); Timothy J. Danielson, Monument, CO (US); Roman Janer, Englewood, CO (US)

(73) Assignee: Hologic Inc, Bedford, MA (US)

( * ) Notice: Subject to any disclaimer, the term of this patent is extended or adjusted under 35 U.S.C. 154(b) by 721 days.

(21) Appl. No.: 11/658,952

(22) PCT Filed: Jul. 29, 2005

(86) PCT No.: PCT/US2005/027175
§ 371 (c)(1),
(2), (4) Date: Mar. 3, 2010

(87) PCT Pub. No.: WO2006/015296
PCT Pub. Date: Feb. 9, 2006

(65) Prior Publication Data
US 2010/0191104 A1    Jul. 29, 2010

Related U.S. Application Data

(60) Provisional application No. 60/592,740, filed on Jul. 30, 2004.

(51) Int. Cl.
*A61B 5/05* (2006.01)

(52) U.S. Cl.
USPC ........... 600/427; 600/407; 600/437; 600/439; 600/459; 600/461; 382/128; 382/130; 382/131

(58) Field of Classification Search
USPC ........... 382/128, 130, 131; 600/407, 427, 437
See application file for complete search history.

(56) References Cited

U.S. PATENT DOCUMENTS 5,474,072 A    12/1995    Shmulewitz
6,147,678 A *  11/2000    Kumar et al. .................. 345/158
(Continued)

FOREIGN PATENT DOCUMENTS

EP    0776124 A3    3/1998
WO   WO94/21189    9/1994
(Continued)

OTHER PUBLICATIONS

International Search Report from PCT/US05/27175, dated Apr. 12, 2007.

*Primary Examiner* — Baisakhi Roy

(57) ABSTRACT

An apparatus for use in performing imaging a region of a patient's body including a first imaging system for acquiring first imaging information including a first region of interest using a first imaging modality, a second imaging system for acquiring second imaging information including a second region of interest using a second imaging modality, a first drive system for selectively moving at least a portion of one of the first and second imaging systems relative to an imaging reference frame, wherein the first drive system is operative to move one of the first and second imaging systems independent of movement of the other of the first and second imaging systems. A method for imaging a region of a patient's body including acquiring first imaging information corresponding to a first region of interest using a first imaging modality, acquiring second imaging information corresponding to a second region of interest using a second imaging modality, selectively moving at least a portion of one of a first and/or second imaging system relative to an imaging reference frame, wherein selectively moving comprises operating moving one of the first and second imaging systems independent of movement of the other of the first and second imaging systems.

8 Claims, 14 Drawing Sheets

(56) References Cited

U.S. PATENT DOCUMENTS

| | | | |
|---|---|---|---|
| 6,204,852 B1 * | 3/2001 | Kumar et al. | 345/419 |
| 6,205,347 B1 * | 3/2001 | Morgan et al. | 600/407 |
| 6,211,906 B1 * | 4/2001 | Sun | 348/144 |
| 6,302,579 B1 | 10/2001 | Meyer | |
| 6,574,499 B1 | 6/2003 | Dines | |
| 6,674,462 B1 * | 1/2004 | Ooshima et al. | 348/42 |
| 6,928,142 B2 | 8/2005 | Shao | |
| 6,990,220 B2 * | 1/2006 | Ellis et al. | 382/128 |
| 7,078,720 B2 * | 7/2006 | Yamaguchi | 250/559.38 |
| 7,103,205 B2 | 9/2006 | Wang | |
| 7,146,049 B2 * | 12/2006 | Flotats et al. | 382/218 |
| 7,250,922 B2 * | 7/2007 | Sakaniwa | 345/1.3 |
| 7,423,666 B2 * | 9/2008 | Sakakibara et al. | 348/136 |
| 2001/0021244 A1 * | 9/2001 | Suzuki et al. | 378/196 |
| 2003/0149364 A1 | 8/2003 | Kapur | |
| 2003/0152490 A1 * | 8/2003 | Trulson et al. | 422/99 |
| 2003/0194050 A1 | 10/2003 | Eberhard et al. | |
| 2004/0068170 A1 | 4/2004 | Wang | |
| 2004/0076262 A1 | 4/2004 | Shao | |
| 2005/0089205 A1 * | 4/2005 | Kapur et al. | 382/128 |
| 2008/0091103 A1 * | 4/2008 | Sundar et al. | 600/439 |
| 2008/0285795 A1 * | 11/2008 | Maddison et al. | 382/100 |

FOREIGN PATENT DOCUMENTS

| | | |
|---|---|---|
| WO | WO95/011627 | 4/1995 |
| WO | WO96/35372 | 11/1996 |
| WO | WO03/054577 A1 | 7/2003 |
| WO | WO2004/036250 A1 | 4/2004 |

* cited by examiner ically to an imaging device for fused mammography with
independently moveable modalities.

IMAGING DEVICE FOR FUSED MAMMOGRAPHY WITH INDEPENDENTLY MOVEABLE IMAGING SYSTEMS OF DIFFERENT MODALITIES

CROSS-REFERENCE TO RELATED APPLICATIONS

This application claims the benefit of U.S. Provisional Application No. 60/592,740, filed Jul. 30, 2004.

FIELD

Embodiments of the present invention relate generally to breast screening in fused mammography, and more specifically to an imaging device for fused mammography with independently moveable modalities.

BACKGROUND

In the field of medical imaging, various modalities are available, such as magnetic resonance imaging (MRI) and computed tomography (CT). Fusion (e.g., combined use) of multiple imaging modalities has been employed for the past decade and is still in its infancy stage. MR and CT were fused first, due in part to the digital nature of these modalities. Conventional systems that employ fusion have drawbacks that arise in part because of technical aspects related to multiple modalities.

Some problems with conventional coupled systems that fuse X-ray and ultrasound relate to interaction between the X-ray portion and the ultrasound portion, which results in motion-induced artifacts. For example, the X-ray and ultrasound systems are typically physically close to each other, such that movement of the breast tissue caused by ultrasound vibrations can render the breast tissue unsatisfactorily unstable when the X-ray scan is scanning a nearby portion of the tissue. In addition, the two systems are mechanically linked, which can cause disturbances in the motion system that can be difficult to compensate for. Such disturbances can be large in magnitude and of relatively high frequency content. Furthermore, because the X-ray and ultrasound systems are coupled, it can be difficult to remove the non-scanning detector from the scan area. As such, the ultrasound and X-ray systems of conventional systems cannot scan as large an area as might otherwise be possible.

SUMMARY

An apparatus for use in performing medical procedures on a patient's breast including structure for immobilizing a patient with respect to an imaging reference frame, a first imaging system for acquiring first imaging information including a first region of interest using a first imaging modality, a second imaging system for acquiring second imaging information including a second region of interest using a second imaging modality, a first drive system for selectively moving at least a portion of one of said first and second imaging systems relative to said imaging reference frame, wherein said first drive system is operative to move one of said first and second imaging systems independent of movement of the other of said first and second imaging systems.

A method for imaging a patient's breast including immobilizing the patient's breast with respect to an imaging reference frame; acquiring first imaging information corresponding to a first region of interest using a first imaging modality, said acquiring first imaging information comprising scanning with a first imaging system, acquiring second imaging information corresponding to a second region of interest using a second imaging modality, said acquiring second imaging information comprising scanning with a second imaging system, selectively moving at least a portion of one of said first and second imaging systems relative to said imaging reference frame, wherein selectively moving comprises operating a first drive system to move one of said first and second imaging systems independent of movement of the other of said first and second imaging systems.

DETAILED DESCRIPTION

Figure 1:
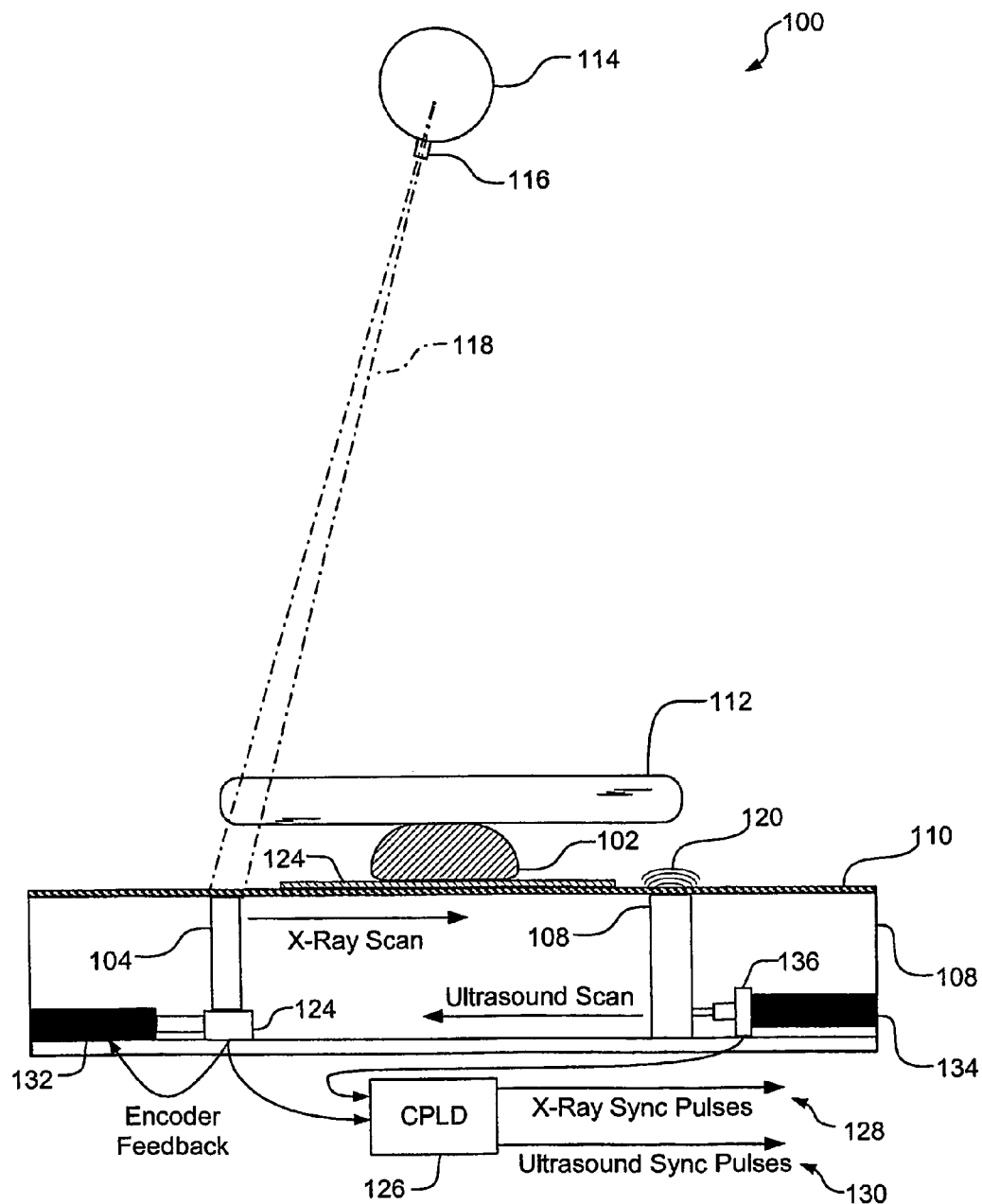
FIG. 1 is a schematic diagram illustrating an exemplary imaging apparatus using ultrasound (US) and X-ray imaging in accordance with one embodiment.

Embodiments of methods and systems are described herein that facilitate the acquisition of breast images using at least two different imaging modalities. Such imaging modalities may include, inter alia, ultrasound (US), X-ray, CT and/or MRI. As will be appreciated, images from two or more of these different imaging modalities may be integrated (e.g., fused) to provide an enhanced image for mammography screening (e.g., lesion detection), biopsy, etc. Beneficially, images acquired using these embodiments are substantially artifact free in all of the imaging modalities. More particularly, embodiments provide separate imaging modalities that may be operated independent of one another.

In accordance with some embodiments, computer aided diagnosis (CAD) can be used between two modalities. Thus, the CAD design may be utilized to steer the second image modality acquisition. In addition, some embodiments include an on-line fast lesion detection system carried out between the two modalities for narrow breast region screening and diagnosis. Embodiments exhibit low system noise due to an independent motor design.

In other embodiments the speed of the fused mammography system is increased over conventional systems. In this regard, the scanning of a second image modality (e.g., ultrasound) can be performed directly after a return stroke of a first imaging modality (e.g., X-ray). Hence the system is faster than the conventional systems.

Certain embodiments include a single gantry design. In these, both of the image acquisition modalities may be designed to use one gantry as a support structure.

In accordance with some embodiments of an imaging apparatus, a mechanical link can be provided efficiently, which may link, for example, an X-ray system tube with a motion system of the imaging apparatus.

Various embodiments of systems include easily designed fusion software. Because an exemplary system yields a simple X-geometry, an ultrasound projection image is easily computable from a 3-D ultrasound volume. Thus, the fusion software can be easily designed.

According to some embodiments, the system is a software-based fusion diagnostic system in which one modality is acquired in 3 dimensions and other modality is acquired using 2 dimensional projection. The fusion system can be easily extended to any 3-D methodology such as, but not limited to, magnetic resonance imaging (MRI) or computed tomography (CT).

In certain embodiments image registration is based on a similarity measure when one image is computed using the 3-D volume projection while the other image is computed using plane projection. Because this registration will use images coming from different frameworks, it is very robust. The method can employ the mutual information based strategy. In some embodiments, the registration is done in the multi-resolution framework, which makes the system fast and accurate in convergence.

Embodiments of the system screen a breast by fusing ultrasound with X-rays. This system then demonstrates the fusion of modalities for diagnostic information extraction. Examples of the combined image acquisition system are very general because the 3-D ultrasound can be used off the shelf for 3-D image acquisition when the imaging modalities utilize the de-coupled motor design.

Some embodiments employ a constant velocity profile. The mechanical design is built in such a way that the velocity of the image acquisition is constant over a majority of the imaging acquisition time for each imaging modality. The systems can scan simultaneously as they can each scan at the speeds appropriate for the detector. Beneficially, such simultaneous scanning can shorten the time required for the patient's breast to be compressed. In some embodiments, disturbances that may be caused in the electrical system due to the extra non-periodic forces on the system are minimized. This allows the system to use a simpler control system.

Because embodiments of the system utilize a linear scan mechanism, feedback from the encoder can be more readily available. For example, encoder feedback can be used to generate pulses for the time-delay-integration (TDI) clock. This can result in a smear-free image even if large motion disturbances are encountered that can frustrate maintenance of a constant velocity. Therefore, a lower cost, simpler control mechanism may be used.

In some commercially available (from, e.g., FISCHER IMAGING CORPORATION) integrated systems primary components of the electrical system include one scanning motor that moves both an X-ray camera and ultrasound transducer simultaneously. In such systems, each scan typically requires a different velocity in order to work properly so the X-ray data can be collected on the forward scan and the ultrasound data can be, collected on the reverse scan. The X-ray and ultrasound are typically linked mechanically so that the co-registered images can be created from the data collected. A linear encoder can be attached in such a way so as to ensure that relative positioning of the data from the two scans remain the same each time an image is taken.

FIG. 1 is a schematic diagram illustrating an imaging apparatus 100 using fused ultrasound (US) and X-ray to image a patient's breast 102. Imaging apparatus 100 includes X-ray detector 104 and ultrasound transducer(s) 106, which may be located within a housing 108 having support layer 110. The breast 102 is compressed between support layer 110 and a compression paddle 112. Components of the imaging apparatus 100 are typically enclosed in a housing (not shown) that includes an opening in which the patient can position her breast 102.

The imaging apparatus 100 may include an x-ray radiation source 114, e.g. an x-ray tube, and collimating optics and/or selectable filters 116, for transmitting a focused radiation signal 118. By way of example, the radiation signal 118 may comprise a fan-shaped beam. The radiation source 114 may be disposed for controlled rotation about a fixed axis, wherein the radiation signal 118 may be scanned across a selected region of a patient's body.

X-ray detector 104 and ultrasound imager 106 are disposed beneath the breast 102 for imaging the breast 102 tissue. The X-ray detector 104 receives at least a portion of the radiation signal 118 passing through the breast 102 and provides a digital X-ray image signal in response thereto. The X-ray image can be reconstructed using the digital detector principle. To accommodate x-ray imaging operations, the compression paddle 112 should be radiolucent. For example, a low density, thermoplastic material may be employed. The support layer 110 of housing 108 should be both radiolucent and sonolucent. For example, a low-density thermoplastic having a relatively small x-ray attenuation coefficient may be employed. In one arrangement, a crystalline, or aliphatic, polymer may be utilized, such as a poly 4-methyl, 1-pentene (i.e. PMP) material, e.g. a material commercially available under the product name "TPX" from Mitsui Plastics, Inc., White Plains, N.Y.

Ultrasound imager 106 transmits/receives ultrasound signals 120 into/from the breast 102 and provides a digital ultrasound image signal in response thereto. Breast 102 rests on acoustic coupling means 122. An acoustic coupling means 122 may be utilized to acoustically couple the patient's breast 102 to a topside of support layer 110. For example, a standard ultrasound gel (e.g. a glycerin-based gel) gel or other flowable acoustic couplant may be contained within a pad located in contact with or otherwise applied to either or both of the top and bottom sides of support layer 110. Alternatively, acoustic coupling means 122 may comprise an ultrasound-coupling, solid-disposable membrane, e.g. a SCANTAC membrane offered by Sonotech, Inc. of Bellingham, Wash. As may be appreciated, the use of a gel-containing pad or solid-membrane for acoustic coupling means 122 may reduce or even avoid the need to apply ultrasound couplants directly to a patient's breast 102, thereby reducing set-up and clean-up procedures.

The system of FIG. 1 typically includes an encoder that tracks speed corresponding to the scanning movement. On the forward scan an encoder 124 reads an encoder strip for generating pulses used primarily for feedback to the motion control system. On the reverse scan, the encoder can be used to not only maintain a constant velocity, but also to generate synchronization pulses for the ultrasound system.

The ultrasound system also uses a signal related to the absolute position in order to create a scan that is absolutely related to position. In the coupled X-ray/ultrasound system, this signal is created from the same encoder 124 used for the x-Ray scan. A CPLD (complex programmable logic device) 126 is used to decode the pulses from the encoder 124 and create a stream 128 of pulses corresponding to the X-ray and another stream 130 of pulses corresponding to the ultrasound system. The intervals of the two streams of pulses are typically different. By way of example, but not limitation, the ultrasound system pulses 130 are typically generated at rate of one pulse every 500 μm.

The embodiment of FIG. 1 advantageously de-couples the imaging detectors 104, 106 to eliminate a source of artifacts or substantially reduce the likelihood of introduction of artifacts, thereby facilitating generation of substantially artifact-free image acquisition. The artifact-free images may then be utilized to generate fused images. The artifact-free images thus improve the sensitivity and specificity of the lesion detection process.

Embodiments incorporate a mechanical design enabling independent movement of imaging modalities. In one particular embodiment, as is discussed further hereinbelow, the de-coupled imaging detectors for both medical image modalities are positioned on the same linear guide rails but at two different ends of the field-of-view, or, so-called home positions. In this embodiment, the system uses two independent drive motors (e.g., two ball-screw actuators) for each imaging modality. The independent motors are integrated in a way such that the velocity profile is constant during data acquisition for both imaging modalities. This results in an artifact-free image during the image acquisition process.

In a further embodiment, the mechanical design may involve a first imaging modality (e.g., X-ray) geometry that can be used to compute the projection image of a second imaging modality (e.g., ultrasound). Such a configuration may thus facilitate, for example, ultrasound projection image computation for the fusion process. Accordingly, such a design improves the sensitivity and specificity of the "fused mammography" system.

In addition, embodiments of systems may utilize a linear scan mechanism wherein feedback from the encoder can be more readily used to create pulses for a time-delay-integration (TDI) clock. This results in a spear-free image. Further, the electrical control system is simplified and non-periodic forces are minimized.

In the improved system, in order to achieve constant velocity scanning two separate motion control systems are utilized. For the X-ray scan, a brushless DC motor is used that is served to an optical encoder of high resolution. In this case, the resolution of the encoder is 0.5 μm while a pixel width for the high resolution scan case is equivalent to 27 μm. The X-ray system uses a Time Delay and Integration (TDI) approach in order to achieve excellent resolution with minimal dose. This approach relies on the velocity of the scan to be synchronized with the clock that shifts the data through the CCD array of the camera or the resulting image will be smeared. This synchronization signal can be generated either from a separate clock or from counting encoder pulses. If the encoder pulses are used, the resulting image is not smeared, but any velocity error during the scan may result in some intensity variations in the image. If the synchronization signal from the encoder pulses is used, however, it has the added benefit of providing a pulse that is related to the absolute position of the detector. Exemplary fused systems and methods of use are further described in U.S. Provisional Patent Application No. 60/586,850, filed Jul. 9, 2004, and entitled "Method For Breast Screening in Fused Mammography", and U.S. Provisional Patent Application No. 60/586,669, filed Jul. 9, 2004, and entitled "Diagnostic System for Multimodality Mammography" by Fischer Imaging Corporation, which are incorporated herein by reference for all purposes. The problem has traditionally been that curved scans did not allow for an encoder to be used with enough precision to generate the clock pulses. However, because this system utilizes a flat scanning mechanism, encoders are readily available with enough resolution.

Because the spatial accuracy requirements of the Ultrasound system are typically much lower, the X-ray system and the Ultrasound system can be effectively decoupled and separate encoders used for each, and yet maintain adequate accuracy to create high quality co-registered images.

In conventional systems the velocity requirements related to the two scans were quite different, which meant that data must first be acquired with one system and then the other, which could result in increased scan times. By decoupling the two systems in embodiments described herein, an X-ray scan can be done quickly and the Ultrasound scan can begin as soon as the X-ray detector is out of the way, rather than waiting to complete the scan.

The motion control systems of embodiments described herein are designed so that each of the different modalities is synchronized electrically by using the encoders used for the feedback system. There are two encoders in the system. The first is for the X-ray scan where the encoder outputs pulses based on the absolute position of the camera. The second encoder outputs pulses based on the absolute position of the ultrasound puck (e.g., ultrasound transducer). These two encoder signals are of such resolution that once data has been synchronized using test images that they will remain so on subsequent images.

Accordingly, FIG. 1 illustrates an exemplary decoupled system 100 with a first motor 132 responding to a linear encoder for driving the X-ray scan, and a second motor 134 with a rotary encoder 136 driving the ultrasound 106 scan. An exemplary embodiment of a linear encoder includes an encoder strip having marks encoded thereon, wherein the marks are indicative of the velocity of movement of an imaging detector. Examples of such an encoder strip are described in U.S. Pat. No. 5,917,881, issued to Jeffery and entitled "Digital Scan Mammography Apparatus Utilizing Velocity Adaptive Feedback and Method", which is incorporated herein by reference for all purposes. The rotary encoder 136 is adequate as the mechanics of the motion system are such that additional compensation is not required to achieve the desired resolution. For the X-ray scan, a linear encoder along the scan axis is still desirable in order to more easily maintain the required scan velocities. A single CPLD 126 can be used to generate the synch pulses 128, 130. One embodiment of the CPLD 126 uses two separate modules: an X-ray pulse generation module, and an ultrasound pulse generation module.

Figure 2:
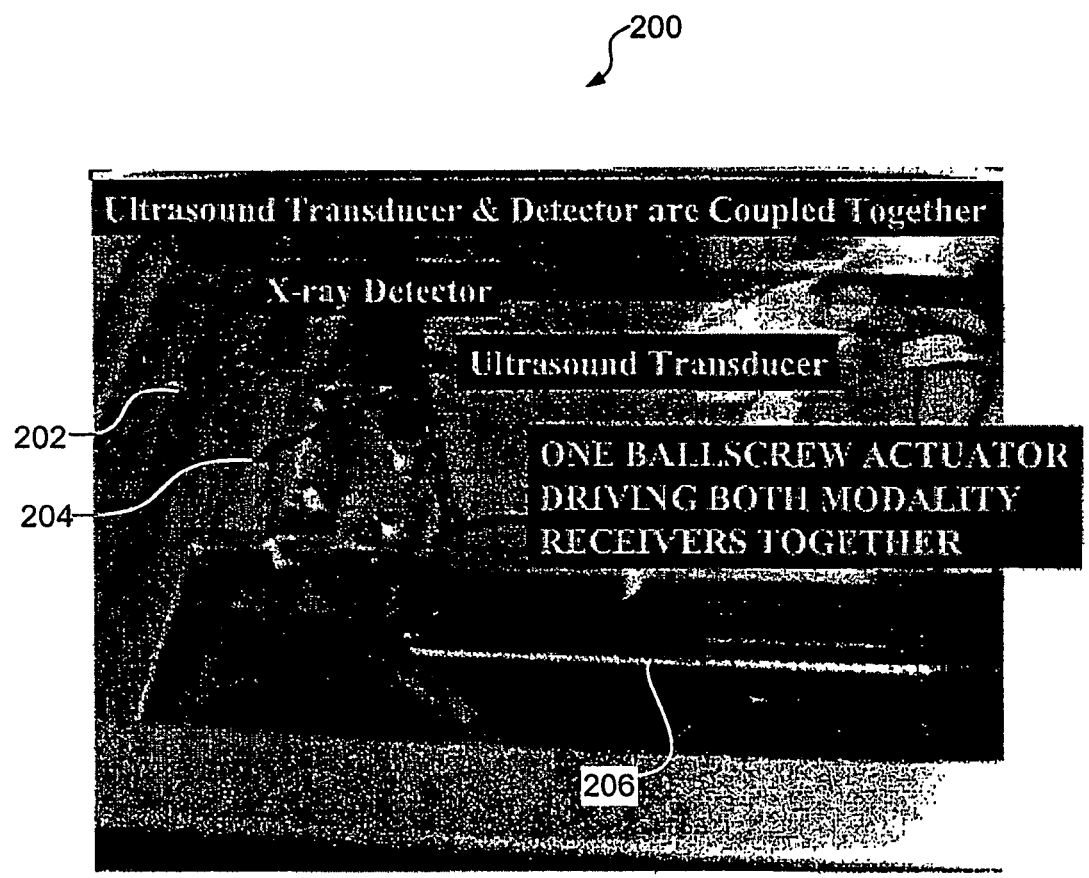
FIG. 2 illustrates another embodiment of an imaging system having an X-ray detector and US transducer, which are mechanically coupled and driven by a common ball screw actuator.

FIG. 2 illustrates another embodiment of an imaging system 200 having an X-ray detector 202 and US transducer 204, which are mechanically coupled and driven by a common ball screw actuator 206.

Figure 3:
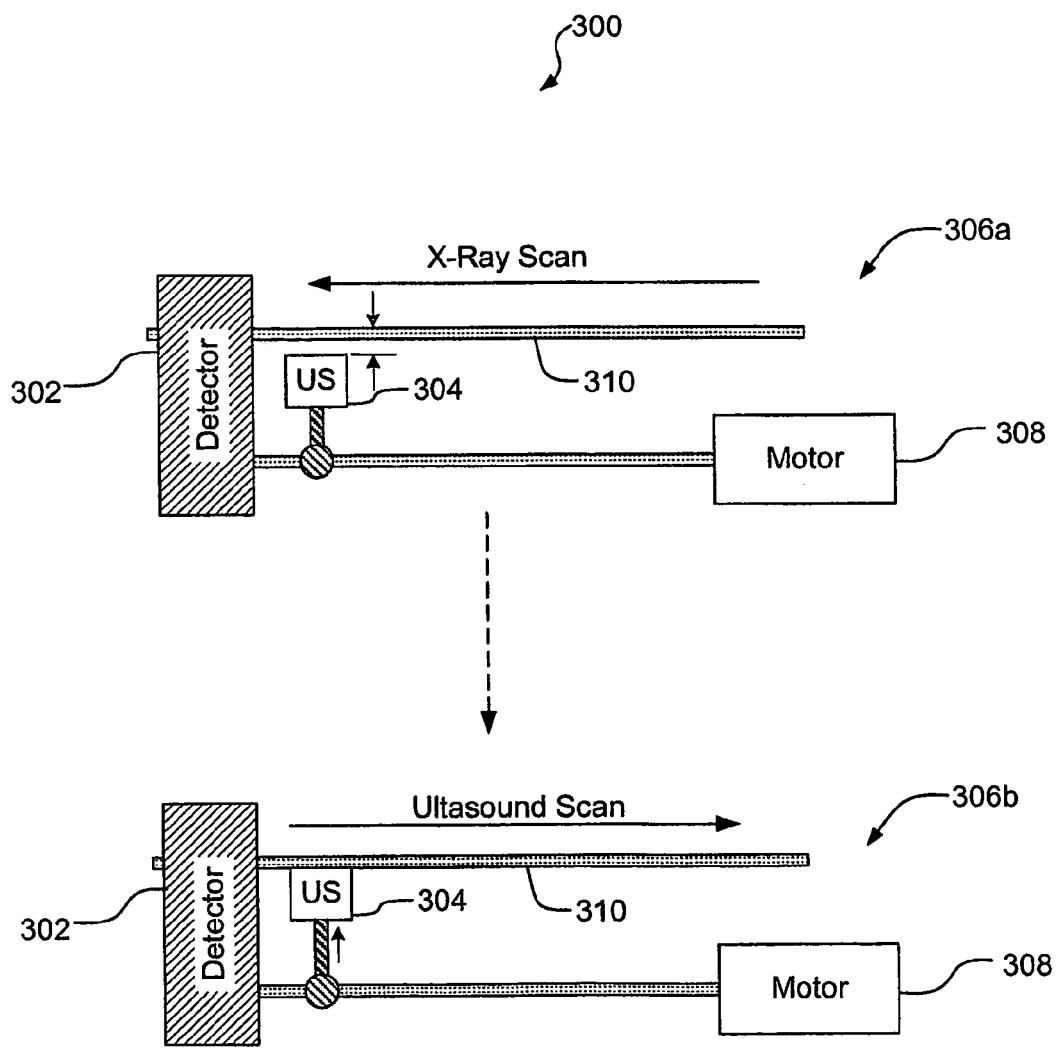
FIG. 3 illustrates one exemplary embodiment of a portion of an imaging system 400 for decoupling the different imaging modalities.

FIG. 3 illustrates one exemplary embodiment of a portion of an imaging system 300 for decoupling the different imaging modalities. In the illustrated embodiment, scanning can be performed by the X-ray imaging device 302 and the ultrasound (US) imager 304. The system 300 is illustrated in two stages of the sequence: an X-ray scanning stage 306a and an ultrasound scanning stage 306b. Although in this embodiment the X-ray detector 302 scans independently of the ultrasound transducer 304, whereby scanning in different modalities can be performed sequentially, in other embodiments the US imager 304 may be interconnected to the X-ray imaging device 302, such that the US device 304 can move during the X-ray scan.

In the embodiment of FIG. 3, a single drive motor 308 is utilized to sequentially drive the X-ray imaging device 302 and US imaging device 304. In particular, in X-ray scanning stage 306; the motor 308 moves the X-ray detector 304 across a support surface 310 while the US device 304 is disengaged from the support surface 310. Once the X-ray scan is done, the X-ray detector 302 is deactivated. In ultrasound scanning stage 306b, the US device 304 is engaged with the support surface 310. The US device 304 may then move across the support surface 310 to perform US scanning.

Figure 4:
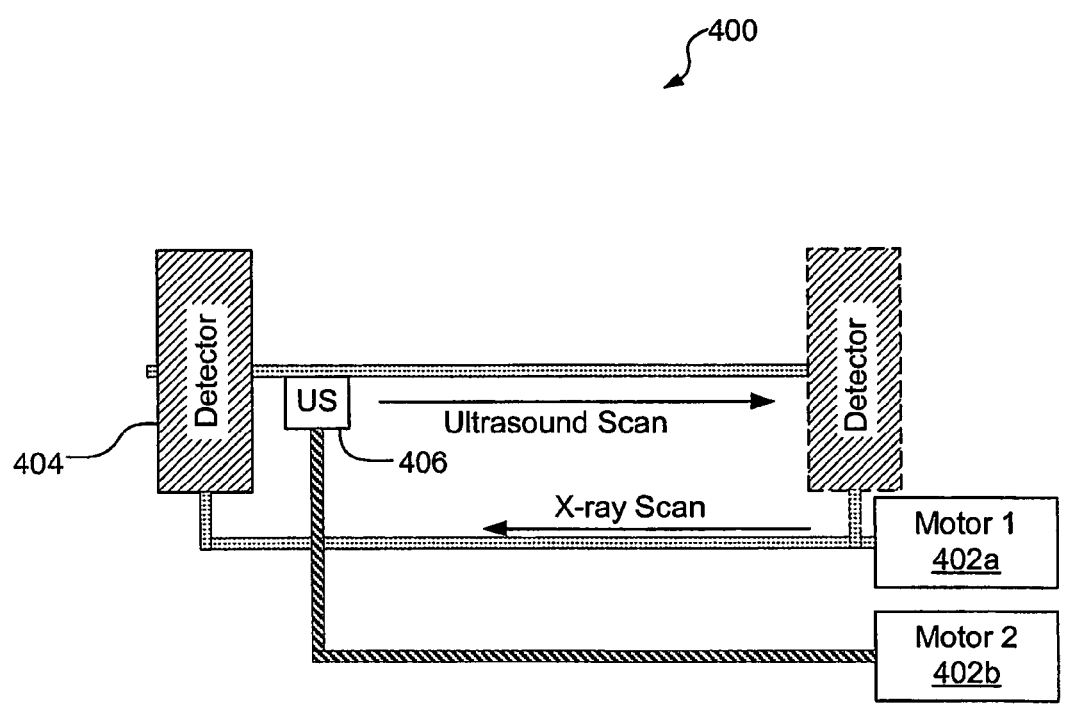
FIG. 4 illustrates another exemplary embodiment of a portion of an imaging system, in which separate drive motors are utilized to separately drive the X-ray detector and the US transducer.

FIG. 4 illustrates another exemplary embodiment of a portion of an imaging system 400, in which separate drive motors 402a, 402b are utilized to separately drive the X-ray detector 404 and the US transducer 406. In this regard, the X-ray detector 404 and US imaging device 406 may be sequentially or simultaneously driven. Advantageously in a computer-aided detection (CAD) system, the arrangement illustrated in FIG. 4 may allow for partial US imaging. For instance, as soon as a lesion is identified during the X-ray scan, the US device 406 may begin imaging of the lesion area. Based on image(s) from the X-ray scan, the region scanned by the US transducer 406 may be limited to only areas of interest (e.g., lesions), thereby reducing the amount of time that is required to scan a patient's breast and thereby reducing patient discomfort.

In either embodiment, the motors 402; 402b may be configured to provide constant velocity movement such that images from the different modalities (e.g., X-ray and US) may be accurately fused. In this regard, the motors 402; 402b provide a short "ramp-up" period after which they provide for substantially constant velocity movement during image acquisition. Finally, it will be noted that the use of separate motors 402; 402b allows for optimizing the scanning velocity for a given imaging modality.

Figure 5:
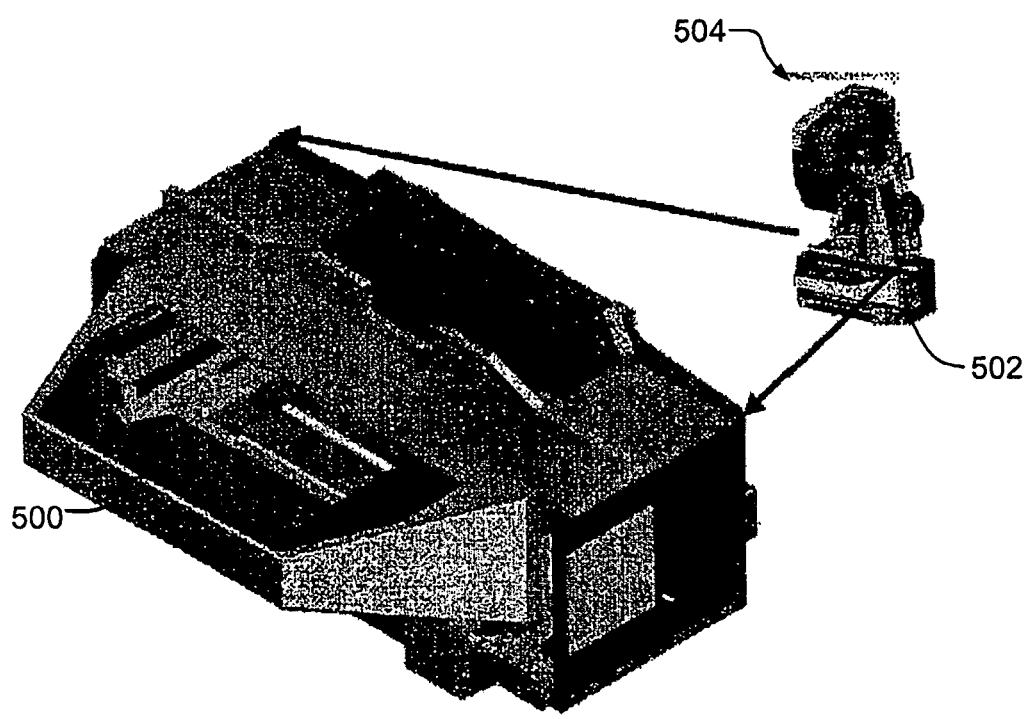
FIG. 5 illustrates an embodiment of a lower breast support that may be utilized in a lower gantry.

FIG. 5 illustrates an embodiment of a lower breast support 500 that may be utilized in a lower gantry 502 of a breast imaging device 504 and which may house decoupled detectors of the imaging devices.

Figure 6:
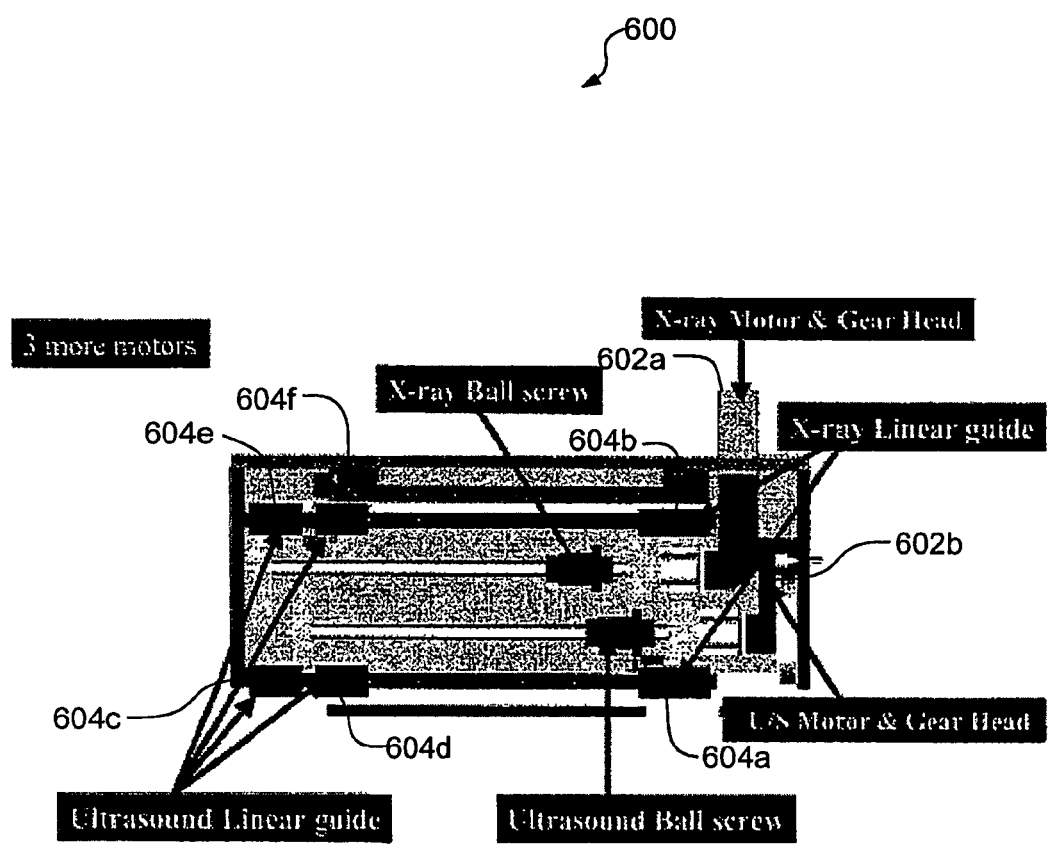
FIG. 6 is a plan view of one embodiment of the interior of the gantry of FIG. 5.

FIG. 6 is a plan view 600 of one embodiment of the interior of the gantry 502 of FIG. 5. As shown, this embodiment uses separate drive motors 602a, 602b to move the US device and X-ray device, respectively. During operation each imaging device is interconnected to common guide rails 604a-604b using linear guides 608a-608f. The guide rails 608a-f allow the imaging devices to move across the support surface of the gantry 502. In the present embodiment, the imaging devices share a common set of guide rails, however, it will be appreciated that this is not required. Further, in the present embodiment, the imaging devices are initially disposed at opposing ends of the guide rails 604a-f (i.e., home positions). In some embodiments, the US portion of the imaging system further utilizes a third motor for raster scanning purposes as is discussed herein.

Figure 7:
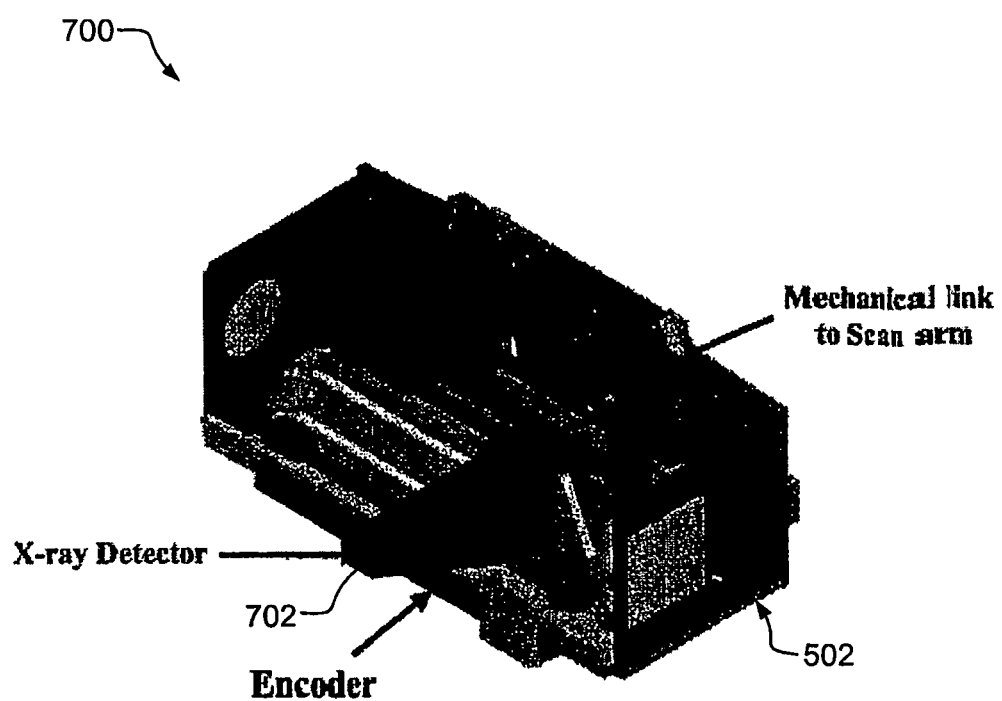
FIGS. 7 and 8 are a perspective view and a plan view, respectively, of an embodiment of the lower gantry.
Figure 8:
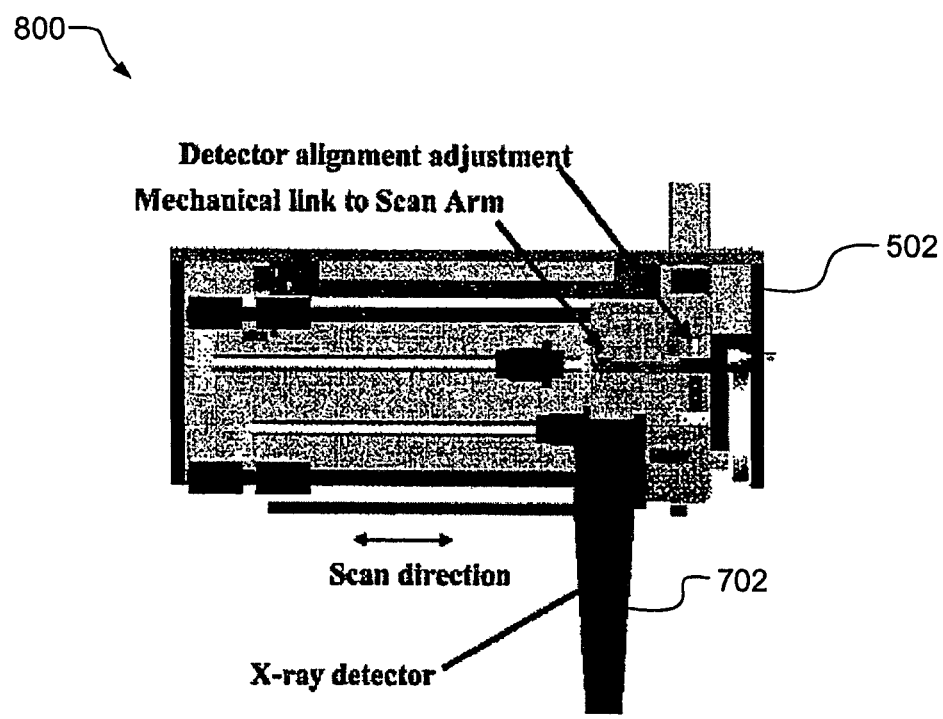

FIGS. 7 and 8 are a perspective view 700 and a plan view 800, respectively, of an embodiment of the lower gantry 502. Views 800 and 900 illustrate one exemplary arrangement for mechanically linking an X-ray tube (not shown) to the lower gantry 502. Referring briefly to FIG. 1, it will be noted that the X-ray tube 114 is disposed above the gantry and turns in an arc during scanning. In the embodiments shown in FIGS. 7 and 8, a mechanical link interconnects the X-ray detector 702 in the gantry 502 with the X-ray tube. In this regard, the motor that drives the X-ray detector 702 in the gantry may also control the rotation of the X-ray source/tube. Of further note, the embodiment of FIG. 7 includes a flexible wiring conduit to route wiring between the imaging detectors in the gantry 502 and the processing platform of the device. Importantly, the conduit prevents any wires from being present in the field of view of the imaging devices.

Figure 9:
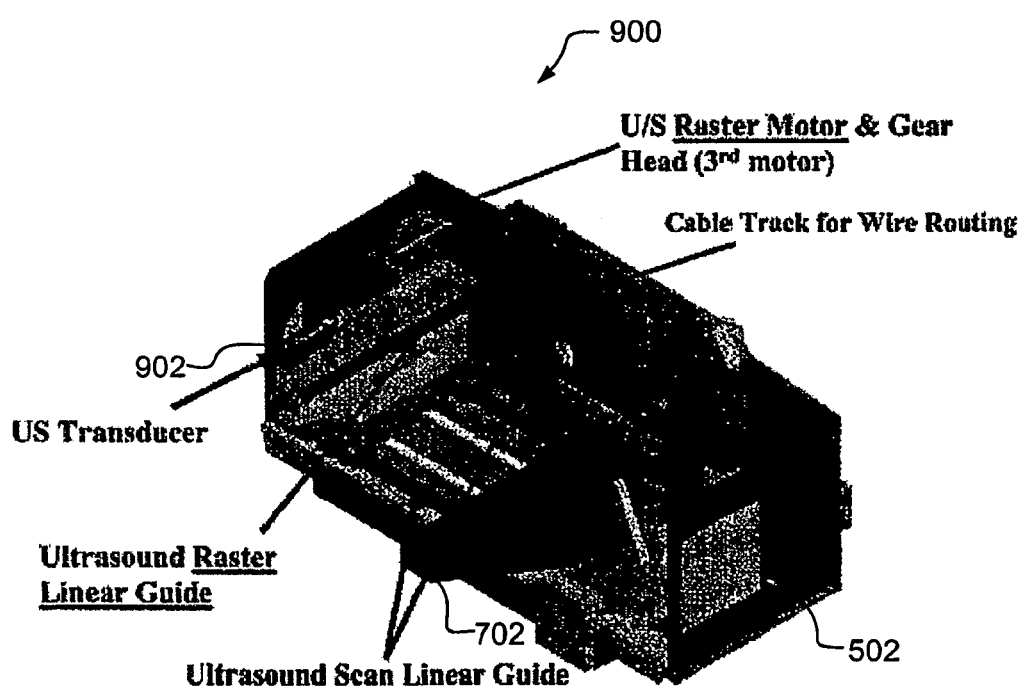
FIGS. 9 and 10 in conjunction with FIG. 6 illustrates an exemplary use of a third motor for use in moving the US detector in a raster pattern.
Figure 10:
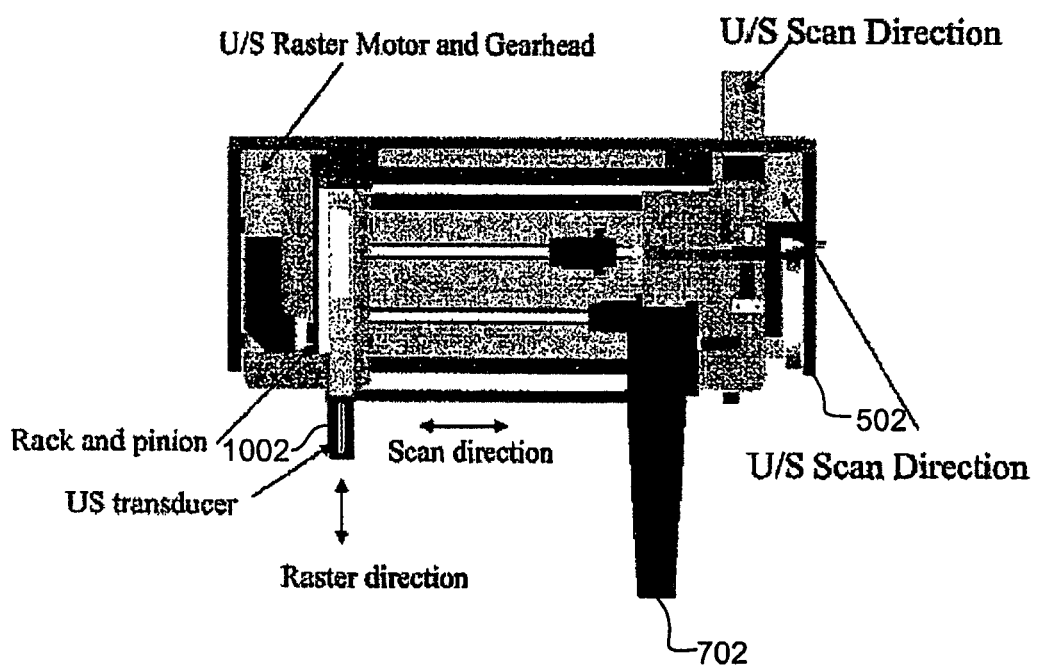

FIGS. 9 and 10 in conjunction with FIG. 6 illustrate an exemplary use of a third motor 900 for use in moving the US transducer 902 in a raster pattern during scanning. However, it will be appreciated that if a detected lesion is small enough, a single US 902 scan may be sufficient for imaging purposes and a raster pattern may not be necessary.

Figure 11:
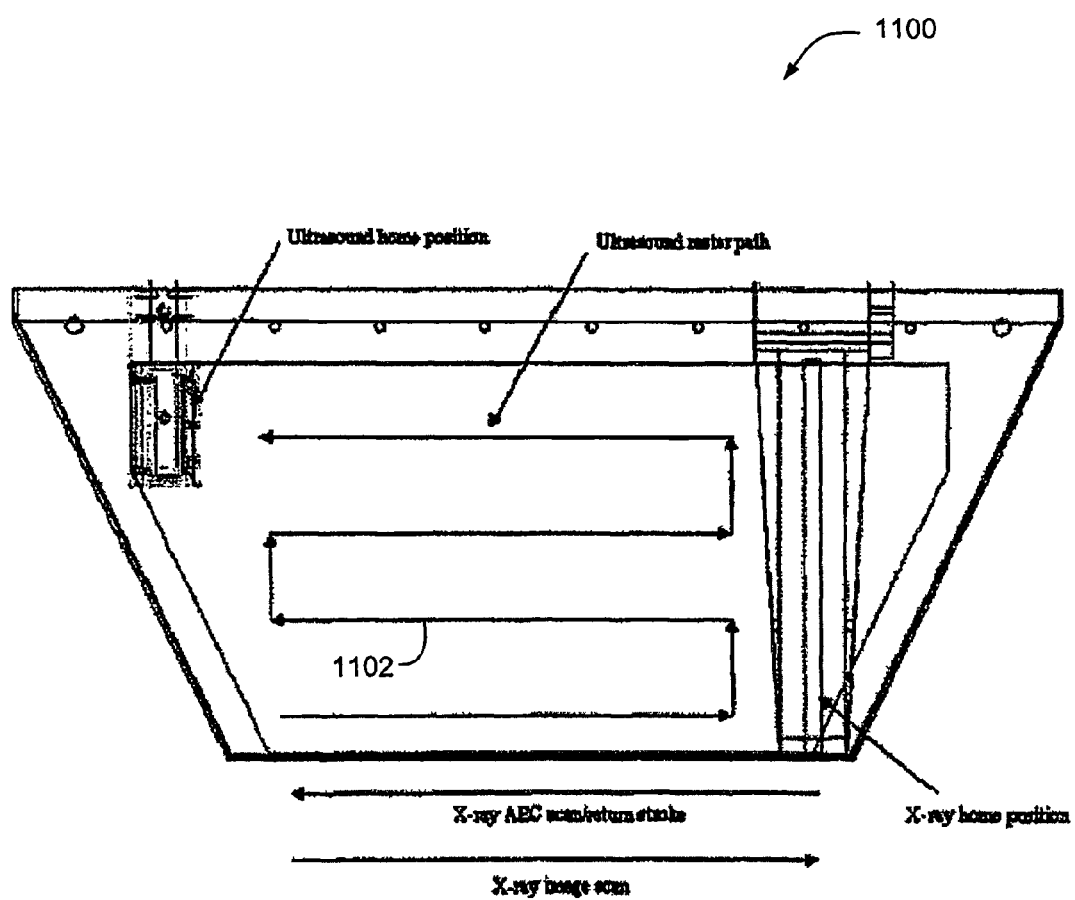
FIG. 11 is a plan view of the top surface of the gantry, illustrating an exemplary raster path that can be followed by at least one type of imaging device.

FIG. 11 is a plan view 1100 of the top surface of the gantry, illustrating an exemplary raster path 1102 that can be followed by at least one type of imaging device. In the particular embodiment shown, an ultrasound imager follows the raster path 1102. Other useful path patterns that may be followed by an imaging device, besides a raster path, may be identified by those skilled in the art, such as, but not limited to, a spiral pattern or a radial pattern.

Figure 12:
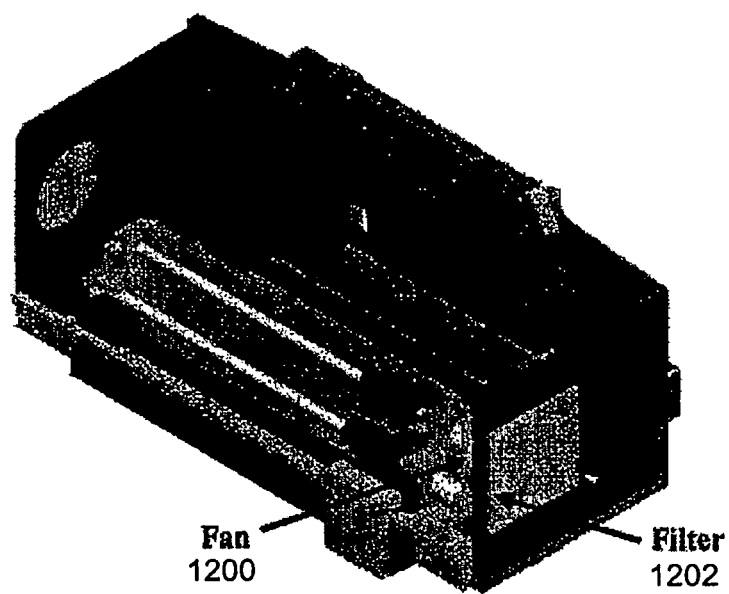
FIGS. 12-14 illustrate additional components of an embodiment of the imaging system.
Figure 13:
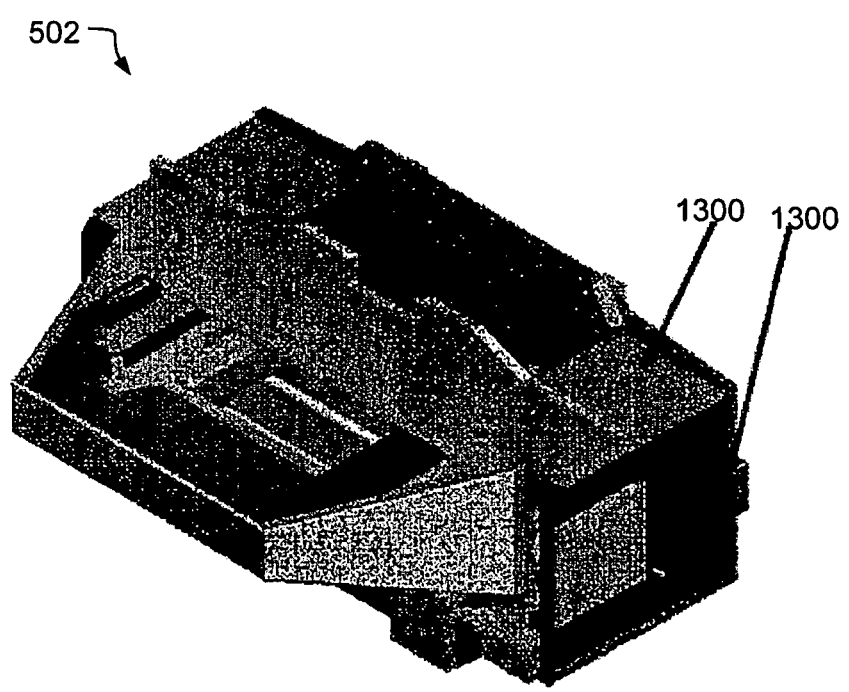
Figure 14:
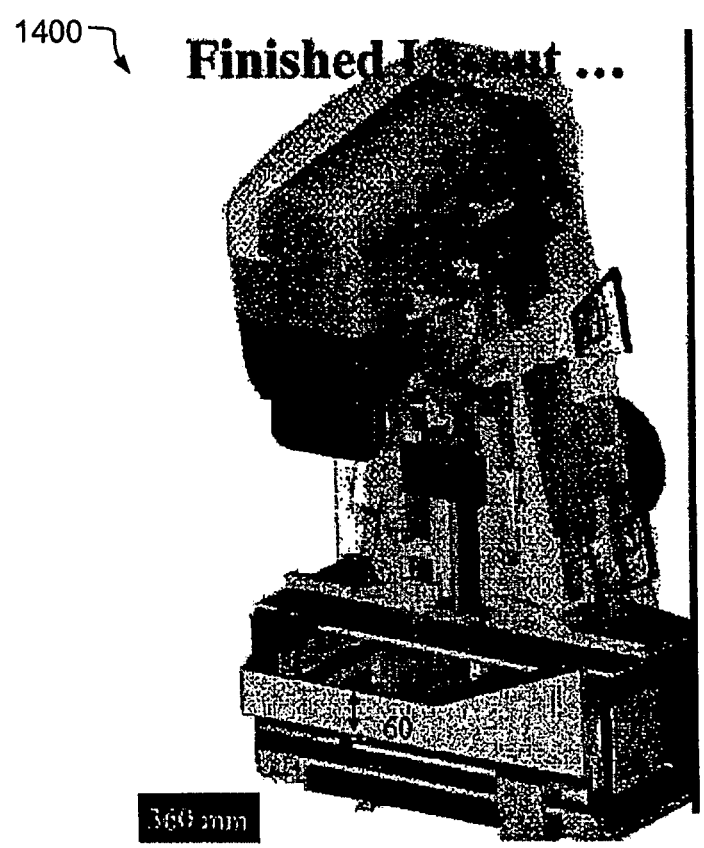

FIGS. 12, 13 and 14 illustrate additional components of an embodiment of the imaging system. For example, FIG. 12 illustrates a fan 1200 and filter 1202. FIG. 13 illustrates plates 1300 for the lower gantry 502. FIG. 14 illustrates an exemplary embodiment of the imaging system 1400 with exemplary dimensions. Further description can be found in the attached Appendix A.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method for imaging a region of a patient's body, the method comprising:

immobilizing a portion of the patient's body with respect to an imaging reference frame;

acquiring first imaging information corresponding to a first region of interest using a first imaging modality, said acquiring first imaging information comprising scanning with a first imaging system mounted on a platform;

acquiring second imaging information corresponding to a second region of interest using a second imaging modality substantially simultaneously with acquiring said first imaging information using said first imaging modality, said acquiring second imaging information comprising scanning with a second imaging system mounted on said platform;

first selectively moving at least a portion of one of said first and second imaging systems relative to said imaging reference frame, wherein first selectively moving comprises moving one of said first and second imaging systems independent of movement of the other of said first and second imaging systems on said platform on a common movement path relative for said first and second imaging systems, said first and second imaging systems operative to move solely along said common movement path relative to said imaging reference frame, said first and second imaging systems being positioned at opposing ends of said common path when said first and second imaging systems are not in use; and simultaneously or sequentially with said first selectively moving, second selectively moving at least a portion of one of said first and second imaging systems relative to said imaging reference frame, wherein said second selectively moving comprises moving one of said first and second imaging systems independently of movement of the other of said first and second imaging systems.

2. The method of claim 1, wherein said first and second selectively moving comprises moving said first and second imaging systems with a constant velocity.

3. The method of claim 1, wherein at least one of said first and second selectively moving comprises moving at least one of said portions of said first and second imaging systems in a raster pattern.

4. The method of claim 1, wherein scanning with said first imaging system and scanning with said second imaging system are accomplished utilizing a single motor.

5. The method of claim 1, wherein said second imaging information corresponding to a second region of interest, corresponds to a subset less than a whole of the first region of interest.

6. The method claim 1, further comprising using a computer-aided detection (CAD) system between scanning with said first imaging system and scanning with said second imaging system.

7. The method of claim 1, wherein said second imaging information is acquired directly after a return stroke of the first imaging system.

8. The method of claim 1, wherein at least one of the first imaging system or the second imaging system comprises an array of detectors that shift during image acquisition, said shifting being driven by a time delay integration (TDI) clock.

* * * * *